US006440902B1

(12) United States Patent
Szamosi

(10) Patent No.: US 6,440,902 B1
(45) Date of Patent: Aug. 27, 2002

(54) COMBINATION OF TWO OR MORE ACTIVE INGREDIENTS USING MICROENCAPSULATED FORMULATIONS

(75) Inventor: Janos Szamosi, Washington, NJ (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 09/374,735

(22) Filed: Aug. 13, 1999

Related U.S. Application Data

(60) Provisional application No. 60/096,973, filed on Aug. 18, 1998.

(51) Int. Cl.⁷ .................. A01N 43/36; A01N 43/647
(52) U.S. Cl. ........................... 504/138; 504/139
(58) Field of Search ................. 504/140, 118, 504/138, 139

(56) References Cited

U.S. PATENT DOCUMENTS

| 5,583,090 A | | 12/1996 | Stern et al. | |
| 5,597,780 A | * | 1/1997 | Lee et al. | 504/271 |
| 5,783,520 A | * | 7/1998 | Anderson et al. | 504/140 |

FOREIGN PATENT DOCUMENTS

| DE | 19635074 | * | 3/1998 |
| EP | 0017409 | | 10/1980 |
| WO | WO 90/08468 | | 8/1990 |
| WO | WO 95/13698 | | 5/1995 |

\* cited by examiner

*Primary Examiner*—Alton Pryor
(74) *Attorney, Agent, or Firm*—FMC Corporation

(57) ABSTRACT

Provided is a method of encapsulating clomazone and a second biological agent comprising: (a) mixing (i) an aqueous phase, (ii) an emulsifier and (iii) a water-immiscible phase containing clomazone, the second biological agent, and at least one first polyfunctional compound; (b) forming a dispersion of water-immiscible droplets throughout the aqueous phase; and (c) adding at least one second polyfunctional compound into the dispersion and reacting the second polyfunctional compound(s) with the first polyfunctional compound(s) to form a polymer shell around the water-immiscible droplets. Further provided is a method of preparing an agricultural composition comprising encapsulated clomazone and a second biological agent, the method comprising:

(a) providing a suspension of clomazone capsules comprising solutes, diluents or carriers;

(b) providing a composition of suspended particles of the second biological agent;

(c) adjusting solutes, diluents or carriers in the particle suspension so that the osmolarity of the particle suspension is sufficiently like that of the capsule suspension so that the capsules are not disrupted when the suspensions of steps (a) and (b) are mixed; and (d) mixing the suspensions of steps (a) and (b).

9 Claims, No Drawings

COMBINATION OF TWO OR MORE ACTIVE INGREDIENTS USING MICROENCAPSULATED FORMULATIONS

This application claims benefit of U.S. Provisional Application No. 60/096,973, filed Aug. 18, 1998.

The present application relates to the field of active ingredient formulations for use in agricultural or pharmaceutical applications.

Microencapsulated formulations have been developed to answer issues concerning controlled release, volatility, or toxicity of certain active ingredients, thereby providing a means for using such ingredients. Formulations of this type that have been described for the herbicide clomazone (see U.S. Pat. No. 5,597,780), for example, are fragile when in concentrated form. The fragility of the microcapsules interferes with preparing concentrated compositions containing with a second component, because the preparation process tends to release the formerly microencapsulated active ingredient. The present invention describes methods and materials for making such two component concentrates. Also, hitherto microcapsules having two or more different active ingredients have not been described. The present invention provides methods and materials for making such two component microcapsules.

SUMMARY OF THE INVENTION

The invention provides a method of encapsulating clomazone and a second biological agent comprising:

mixing (i) an aqueous phase, (ii) an emulsifier and (iii) a water-immiscible phase containing clomazone, the second biological agent, and at least one first polyfunctional compound;

forming a dispersion of water-immiscible droplets throughout the aqueous phase; and adding at least one second polyfunctional compound into the dispersion and reacting the second polyfunctional compound(s) with the first polyfunctional compound(s) to form a polymer shell around the water-immiscible droplets.

The first or second polyfunctional compounds are "polyfunctional" in the sense that each has the capacity to react to form a covalent bond with two or more compounds of the same class as the other polyfunctional compound. For instance, the first polyfunctional compound can be a polyfunctional isocyanate, while the second polyfunctional compound can be an amine.

Also provided is an agricultural composition comprising capsules containing, together, clomazone and a second biological agent.

The invention further provides a method of preparing an agricultural composition comprising encapsulated clomazone and a second biological agent, the method comprising:

(a) providing a suspension of clomazone capsules comprising solutes, diluents or carriers;

(b) providing a composition of suspended particles of the second biological agent;

(c) adjusting solutes, diluents or carriers in the particle suspension so that the osmolarity of the particle suspension is sufficiently like that of the capsule suspension so that the capsules are not disrupted when the suspensions of steps (a) and (b) are mixed; and (d) mixing the suspensions of steps (a) and (b).

In one embodiment, the method further comprises:

(e) milling composition of suspended particles at least until the particles are no more than about 100 μm, in some cases as small as 1 μm, in size.

Accordingly, also provided is an agricultural composition comprising an aqueous suspension of (a) capsules of clomazone and (b) particles, which are distinct from the clomazone capsules, comprising a second biological agent.

DEFINITIONS

The following terms shall have, for the purposes of this application, the respective meanings set forth below.

Agricultural agent shall mean a bioactive agent used in agriculture, such as a herbicide, insecticide or fungicide.

Bioactive agent shall mean a substance such as a chemical that can act on a cell, virus, organ or organism, including but not limited to insecticides, fungicides and herbicides, which substance creates a change in the functioning of the cell, virus, organ or organism.

A particle (which may be liquid) containing a bioactive agent is encapsulated if it is coated with or admixed with an amount of polymer which slows release of the encapsulated agent, reduces the toxicity of the agent to mammals, stabilizes the form of the agent, inhibits crystallization of the agent, reduces the volatility of the agent or produces any other benefit of coating a chemical agent with a polymer or admixing the chemical agent with the polymer.

A microcapsule shall mean an encapsulated particle which is no more than about 1,000 μm in size, preferably no more than about 20 μm in size.

A particle size limit for a composition shall mean that at least about 90% of the particles in the composition shall be within the size range cited, where size is measured by light scattering using an instrument, such as a Laser Scattering Particle Size Distribution Analyser, Horiba Instrument Corp., Irvine, Calif.

The use of the modifier "about" with respect to pH is used herein to indicate a variance of at least one half a pH unit, and preferably indicates a variance of one half a pH unit. In other contexts herein where the modifier "about" is used to qualify a non-log unit, the "about" is intended to indicate a variance of ±15%, yet more preferably a variance of ±10%.

DETAILED DESCRIPTION OF THE INVENTION

A first embodiment of the invention involves the co-microencapsulation of clomazone and another agricultural agent such as a herbicide (for example, dimethachlor). In one preferred embodiment, the co-microencapsulated formulations of the invention are made according to the following steps:

mixing (i) an aqueous phase, (ii) an emulsifier and (iii) a water-immiscible phase (also referred to as an "organic" phase) containing clomazone, a second agricultural agent, and a polyfunctional isocyanate;

forming a dispersion of water-immiscible droplets throughout the aqueous phase; and adding an amine, preferably a polyfunctional amine, into the dispersion and reacting the amine with the polyfunctional isocyanate to form a polyurea shell around the water-immiscible droplets.

Note that while an amine can be a "polyfunctional compound" as described above, the term "polyfunctional amine" refers to compounds with two or more amine functional groups. In a particular embodiment, the invention can comprise the steps of (a) preparing an aqueous phase containing an emulsifier and an antifoam agent; (b) preparing a water-immiscible phase containing clomazone, a second agricultural agent, and a polyfunctional isocyanate; (c) emulsifying the aqueous phase with the water-immiscible phase to form a dispersion of water-immiscible droplets throughout the aqueous phase; and (d) agitating the dispersion while adding to it, either neat or in an aqueous solution, an amine or mixture of amines, thus forming a polyurea shell around the water-immiscible droplets. Once the microcapsules are formed, the suspension can be cured, i.e., incubated over time under polymerization supporting conditions, including, for example, moderate heating. One or more additives, such as propylene glycol, xanthan gum, urea, bactericides, amphoteric surfactants, dyes or ionic dispersing agents (e.g., alkyl naphthalene sulfonate), can be added to the microcapsules. The pH of the formulation is then, in some preferred embodiments, adjusted to neutral, e.g. about pH 6.5 to about 7.5, for example, to improve stability.

The clomazone/herbicide combination is preferably at a ratio of from about 1 to about 20 (~1:~20) to about 20 to about 1 (~20:~1) clomazone to herbicide. For example the ratio of clomazone to dimethachlor can be about 1 to about 12.5 clomazone to dimethachlor. In addition the clomazone/herbicide combination can be, for example, about 5 to about 40, preferably about 31.0, weight percent of the total formulation.

The co-microencapsulated formulations can contain, for example, one or more of the following additional components in the following amounts (in weight percent) based on the total weight of the formulation: 1) emulsifier—up to about 1.5, preferably about 1, weight percent; 2) antifoam agent—up to about 0.5, preferably about 0.25, weight percent; 3) polyfunctional isocyanate—about 2 to about 5, preferably about 4, weight percent; 4) polyfunctional amine—about 1.5 to about 4, preferably about 2.4, weight percent; 5) water—about 40 to about 60, preferably about 45 (such as about 45.1), weight percent. Example 1 illustrates the process for preparing the co-microencapsulated formulations of the present invention.

Preferably, the capsules formed by the polyurea shell are about 1 $\mu$m to about 100 $\mu$m, more preferred about 1 $\mu$m to about 20 $\mu$m.

Preferably, the polyfunctional isocyanate favors partitioning to the water-immiscible phase over the aqueous phase. While preferably the polyfunctional isocyanate favors partitioning into the immiscible phase, preferably such partitioning is not as strong as the partitioning by clomazone. Appropriate polyfunctional isocyanates include, for example, polymethylene polyphenyl isocyanate (PMPPI), 4,4'-diphenylmethane diisocyanate, 2,4+-diphenylmethane isocyanate, hexamethylene diisocyanate and methane diisocyanate. Preferably, the polyfunctional isocyanate is a difunctional isocyanate such as a bis compound. Appropriate amines include, for example, hexamethylene diamine (HMPA), triethylamine, dimethylamine, diethylenetriamine and triethylene tetramine. Preferably, the polyfunctional amine is hexamethylene diamine.

Appropriate herbicides for use as the second agricultural agent include, for example, dimethachlor (2-chloro-N-(2,6-dimethylphenyl)-N-(2 -methoxyethyl)acetamide), pendimethalin (N-(1-ethylpropyl)-3,4-dimethyl-2,6 dinitrobenzamine) and trifluralin (2,6-dinitro-N,N-dipropyl-4-(trifluoromethyl)benzenamine).

Preferably, the curing process comprises heating from about 15° C. to about 60° C., more preferably about 25° C. to about 50° C., for from about 30 minutes to about ten hours, preferably about 1 to about 2 hours.

A second "premixture" embodiment of the invention involves the preparation of a pre-mixture which comprises a combination of clomazone capsule suspension (CS), which can be a commercially available CS, and a suspension of particles of another agricultural agent, such as without limitation the herbicides sulfentrazone (N-[2,4-dichloro-5-[4-(difluoromethyl)-4,5-dihydro-3-methyl-5-oxo-1H-1,2,4-triazol-1-yl]phenyl]methanesulfonamide), propanil (N-(3,4-dichlorophenyl) propanamide), carfentrazone-ethyl (the ethyl ester of 2-dichloro-5 [4-(difluoromethyl)-4,5-dihydro-3-methyl-5-oxo-1H-1,2,4-triazol-1-yl]-4-fluorobenzenepropanoic acid), or metribuzin (4-amino-6-(1, 1-dimethylethyl)-3-(methylthio)-1,2,4-triazin-5(4H)-one). Ordinarily the microencapsulated formulation would not hold its integrity when combined with a particle suspension; however, as described herein both formulations maintain their integrity after they have been combined. In one preferred embodiment, the pre-mixture formulation is made according to the following steps:

(a) providing a suspension of clomazone capsules comprising solutes, diluents or carriers;

(b) providing a composition of suspended particles (which can be encapsulated) of a second agricultural agent;

(c) adjusting solutes, diluents or carriers in the particle suspension so that the osmolarity of the particle suspension is sufficiently like that of the capsule suspension so that the capsules are not disrupted when the suspensions of steps (a) and (b) are mixed; and (d) mixing the suspensions of steps (a) and (b).

Preferably, the particles comprise a herbicide, which herbicide is preferably distinct from clomazone. Preferably, the particles are sized to no more than about 100 $\mu$m, more preferably no more than about 10 $\mu$m, which sizing prevents damage to the clomazone capsules. In certain embodiments, the method will comprise grinding, milling, abrading or like process (hereafter, "milling") the suspended particles at least until the size requirement is met.

The amount of the clomazone and herbicide present in the pre-mixture depends on the type of herbicide used. In general, the range can be from about 0.1 to about 80 herbicide to clomazone or vice versa depending on the herbicide. For example, when sulfentrazone is used the ratio can preferably be two to one clomazone to sulfentrazone; however when dimethachlor is used the ratio can preferably be 12.5 to one dimethachlor to clomazone. Example 2 illustrates the process for preparing the pre-mixture formulations of the present invention.

The preparation of the particle suspension can, for example, involve the following: a) combining the technical material, a copolymer surfactant, such as a calcium lignosulfonate, an ionic dispersing agent (e.g., alkyl naphthalene sulfonate), an antifoam agent, and water; b) stirring the mixture for 5 minutes to two hours; c) intermittently milling the mixture until the particle size of the mixture is below 10 $\mu$m; and then d) adding additional suitable materials, such as xanthan gum, propylene glycol, and calcium or sodium salts, that are contained in the clomazone CS formulation in order to make the two formulations as similar as possible so that when the two formulations are combined there are no problems. The particle suspension can contain one or more of the above components in the following amounts based on the total weight of the particle suspension: 1) bioactive agent(s) such as agricultural agent (s)—about 2 to about 45, preferably about 30–35 weight percent; 2) antifoam agent—about 0.1 to about 1, preferably about 0.3, weight percent; 3) polymeric surfactant—about 0.1 to about 5, preferably about 4, weight percent; 4) dispersing agent—about 0.1 to about 5, preferably about 0.5, weight percent; 5) water—about 30 to about 90, preferably about 43, weight percent; 6) antifreezes and/or thickeners— about 0.1 to about 9, preferably about 0.1 to 7.5, more preferably 0.1, weight percent; 7) total metal ion salts (such as calcium and/or sodium salts)—about 1 to about 15, preferably about 10, weight percent. Such antifreezes and/or thickeners preferably include, without limitation: 6 a) propylene glycol—about 2 to about 5, preferably about 4.5, weight percent; 6 b) xanthan gum—about 2 to about 4, preferably about 3, weight percent.

The invention having been described hereinabove, is further illustrated in the following examples which are not intended to be limitative in any manner.

EXAMPLE 1

This example sets forth one protocol for preparation of a 250 grams/liter clomazone and dimethachlor capsule suspension (250 CS) formulation, in accordance with the present invention.

A stock mixture of clomazone technical and dimethachlor was prepared by stirring 45.0 grams of technical clomazone and 913 grams of commercially available dimethachlor. The solution was stored for later use.

The aqueous phase for co-microencapsulation was prepared in a four-liter stainless steel beaker by mixing 4.0 grams of a calcium lignosulfonate (Norlig® 11 DA, Ligno-Tech USA, Rothschild, Wis.) and 1.0 gram of a 100% polydimethyl siloxane antifoam agent (Dow Corning® 1520, Dow Corning Corp., Midland, Mich.) in 170 grams of distilled water. The entire mixture was then transferred to a one-liter beaker. The mixture was mixed for one minute at high speed, then a pre-blended solution of 160.0 grams of the clomazone/dimethachlor stock mixture and 16.0 grams of polymethylene polyphenyl isocyanate (PMPPI, Papi® 27, Dow Chemical Co., Midland, Mich.) was added, and the mixture was emulsified for five minutes. The mixture was then placed in a one-liter 3-necked roundbottom flask equipped with a mechanical stirrer, and 9.6 grams of a 70% aqueous solution of hexamethylenediamine (HMDA) in 9.6 grams of water was added during a 30 second period. Upon completion of the addition, the mixture was heated to 60° C. and held for one hour. After this time, the mixture was cooled to 25° C. and 14.0 grams of aqueous 2% xanthan gum (Kelzan® S, Monsanto, St. Louis, Mo.) was added. The formulation was then mixed for about 10 minutes and then stored.

EXAMPLE 2

This example sets forth one protocol for preparation of a pre-mixture clomazone and sulfentrazone formulation, in accordance with the present invention.

A suspension concentrate (SC) formulation of sulfentrazone was prepared by stirring a mixture of 350.0 grams of sulfentrazone technical, 40.0 grams of an nonionic polymeric surfactant (Atlox® 4913, ICI Americas Inc., Wilmington, Del., a subsidiary of Imperial Chemical Industries Surfacants), 5.0 grams of an alkyl naphthalene sulfonate dispersing agent (Atlus® 435, ICI Americas Inc.), and 3.0 grams of a 100% polydimethyl siloxane antifoam agent (Dow Corning® 1520) in 429.5 grams of water for four hours. At the conclusion of this period, the mixture was intermittently milled until the particle size was below 10 μm. Once the particle size was below 10 μm, 45.0 grams of propylene glycol, 30.0 grams of 1% aqueous xanthan gum (Kelzan® S), 50.0 grams of calcium chloride, and 47.5 grams of sodium nitrate were added. Then 772.0 grams of this formulation was transferred to a four-liter stainless-steel beaker. The formulation was stirred for one minute, then 1403 grams of a suspension of clomazone capsules, Command® 3 ME (FMC Corporation, Agricultural Products Group, Philadelphia, Pa.) was added. Upon completion of addition, the formulation was then mixed until uniform (about one hour) and stored.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A method of co-microencapsulating clomazone and a second agricultural agent comprising:

mixing (i) an aqueous phase, (ii) an emulsifier and (iii) a water-immiscible phase containing clomazone, the second agricultural agent, and at least one first polyfunctional compound;

forming a dispersion of water-immiscible droplets throughout the aqueous phase; and adding at least one second polyfunctional compound into the dispersion and reacting the second polyfunctional compound(s) with the first polyfunctional compound(s) to form a polymer shell around the water-immiscible droplets.

2. The method of claim 1, wherein said at least one first polyfunctional compound is a polyfunctional isocyanate.

3. The method of claim 2, wherein said at least one second polyfunctional compound is an amine.

4. The method of claim 1, further comprising:

agitating the dispersion during the adding and reacting step.

5. The method of claim 1, wherein the second agricultural agent is a herbicide.

6. The method of claim 5, wherein the herbicide is dimethachlor.

7. An agricultural composition comprising capsules containing, together, clomazone and a second agricultural agent wherein the agricultural agents are co-microencapsulated.

8. The agricultural composition of claim 7, having the following composition:

clomazone and the second agricultural agent, combined, about 20 to about 40 weight percent;

polyfunctional isocyanate, about 2 to about 5 weight percent;

amine, about 1.5 to about 4 weight percent; and water, about 40 to about 60 weight percent.

9. The composition of claim 8, wherein the composition further comprises.

emulsifier, up to about 1.5 weight percent; and antifoam agent, up to about 0.5 weight percent.

* * * * *

UNITED STATES PATENT AND TRADEMARK OFFICE
CERTIFICATE OF CORRECTION

PATENT NO.     : 6,440,902 B1
DATED          : August 27, 2002
INVENTOR(S)    : Janos Szamosi It is certified that error appears in the above-identified patent and that said Letters Patent is hereby corrected as shown below:

<u>Column 6,</u>
Line 33, after "droplets" insert the words -- wherein both clomazone and the second agricultural agent are within the water-immiscible droplets. --
Line 46, after "together," insert the words -- within the capsules, a combination of --

Signed and Sealed this

Twentieth Day of May, 2003

JAMES E. ROGAN
*Director of the United States Patent and Trademark Office*